United States Patent [19]

Finnerty et al.

[11] 4,455,377
[45] Jun. 19, 1984

[54] CLOTTING ASSAY AND REAGENT THEREFOR

[75] Inventors: Suja P. Finnerty, Arlington Heights; Russell A. Hangos, Round Lake, both of Ill.

[73] Assignee: Cooper Laboratories, Inc., Palo Alto, Calif.

[21] Appl. No.: 375,936

[22] Filed: May 7, 1982

[51] Int. Cl.³ ............................................ G01N 33/86
[52] U.S. Cl. ...................................... 436/69; 424/101; 435/13
[58] Field of Search ............................. 436/69; 435/13

[56] References Cited

U.S. PATENT DOCUMENTS

| | | | |
|---|---|---|---|
| 3,293,134 | 12/1966 | Lenahan | 436/69 X |
| 3,395,210 | 7/1968 | Lenahan | 436/69 X |
| 3,486,981 | 12/1969 | Speck | 436/69 X |
| 3,880,714 | 4/1975 | Babson | 435/13 |

*Primary Examiner*—Sidney Marantz
*Attorney, Agent, or Firm*—Vorys, Sater, Seymour & Pease

[57] ABSTRACT

Blood clotting function assays are improved by the use of a colloidal silica contact activator made by the process comprising (a) contacting an alkali silicate solution with an ion-exchange material for removing alkali metal ions from the silicate solution, and (b) recovering the colloidally dispersed particles from the ion exchange material.

10 Claims, No Drawings

CLOTTING ASSAY AND REAGENT THEREFOR

This invention relates to Hageman factor activating substances used in assays for blood clotting, particularly in methods for determining anticoagulants or blood clotting factors. This invention is especially concerned with improvements in activated partial thromboplastin time (APTT) tests.

APTT tests are conventionally employed in detecting and monitoring blood clotting abnormalities. Such deficiencies may result from genetic deficiencies or autoimmune diseases which result in low levels of plasma protein clotting factors, or from the administration of anticoagulants such as heparin. The practice and interpretation of APTT tests are conventional and well known in the art.

Such tests employ an "activator" for Hageman factor. Hageman factor is a protein involved in the initiation of blood clotting via the intrinsic mechanism. Activation of the Hageman factor initiates the sequence of enzymatic conversions which culminate in the clotting of blood. Accordingly, the activator's function is to stimulate a test sample to clot so that the clottability of the sample can be determined. The clottability of the sample is assayed by the time required to reach a given end point such as viscosity, optical density and the like.

A large number of substances are known to activate the Hageman factor, but very few have been used with any success in clotting tests suitable for commercial sale and routine use. Examples of activators which have been employed in clotting tests include fumed silica particles of 20 to about 60 millimicrons in diameter (U.S. Pat. No. 3,880,714) and solutions of sodium ellagate (U.S. Pat. No. 3,486,981).

Presently available assays for blood clotting function are susceptible to various deficiencies. One assay may be completely satisfactory in one respect, but disadvantageous in other contexts. For example, the water soluble activator sodium ellagate is desirable because it can be provided to the test user in aqueous solutions, and reconstitution or suspension of the activator is unnecessary. Assays using this activator, however have been found to exhibit undesirably high coefficients of variation in day-to-day precision.

The fumed silica activator disclosed in U.S. Pat. No. 3,880,714 performs more satisfactorily, but suffers from the disadvantage that the user must prepare an aqueous suspension of the activator before it is used.

Thus, objects of this invention include improving the performance of blood clotting assays, in particular their reproducibility in use in the clinical laboratory, and making the use of the assays more convenient, in particular in the preparation and use of reagents supplied to perform the assays. Other objects will be apparent from this specification as a whole.

SUMMARY OF THE INVENTION

Applicant has found that the objects of this invention may be achieved in clotting function determinations by using as a Hageman factor activator aqueous colloidally dispersed silica or alumina-coated silica particles having an average diameter of about from 4 to 100 millimicrons, wherein the particles were prepared by a process comprising (a) contacting an alkali silicate solution with an ion-exchange material for removing alkali metal ions from the silicate solution, and (b) recovering the colloidally dispersed particles from the ion exchange material.

A novel reagent is supplied for clotting factor determinations which comprises said silica or alumina-coated silica particles colloidally dispersed in an aqueous suspension with a component having platelet factor activity. This reagent also may include buffers and antimicrobial agents.

DETAILED DESCRIPTION OF THE INVENTION

The particular species of colloidal silica employed herein is critical in achieving a principal object of this invention, that being a stable aqueous reagent which may be filled into containers, included in a kit for conducting clotting assays, and then stored for lengthy periods without precipitating or agglomerating out of colloidal dispersion. Heretofore employed activators such as the Aerosil silica particles used in U.S. Pat. No. 3,880,714 are not stable in colloidal dispersions over such periods and thus must be prepared by the test user from dry reagent. In addition, such previously employed activators have required the presence of a suspending agent such as acacia to maintain the activator particles in homogeneous suspension. This is not the case with the present colloidal silica reagent, which preferably is free of suspending agent.

The colloidal particles used herein may be prepared by the method of U.S. Pat. No. 2,244,325, and they are commercially available in a range of particle diameters. The particles having a mean diameter of about 70 millimicrons exhibit a surface area of less than about 50 $m^2$/gram. They are non-agglomerated, essentially spherical in shape, negatively charged and stabilized with a counter ion such as sodium. While the mean particle diameter can range from about 4 to 100 millimicrons, best results are obtained with particles having diameters in excess of about 50 millimicrons, with 70 millimicrons being preferred. Mixtures of particles having different diameters within the range of 4 to 100 millimicrons can be used.

The alumina-coated silica particles exhibit the chemical characteristics of the alumina coating rather than the silica core. While it is preferred to employ the alumina-coated particles, satisfactory results are obtained with colloidal silica prepared as described above, or with a mixture of both types of particles.

The colloidal particles are supplied in aqueous dispersion in a particle concentration of about from 0.01 to 0.2% w/v, preferably about 0.1% w/v. The concentration of colloidal particles is not critical, and in fact may be varied to be compatible with the instrumentation to be employed and calculated to provide optimal assay results.

The reagent will also contain a platelet substitute. This is a well-known component used in clotting assays; it supplies the platelet factor-like activity needed for clot initiation. Cephalin-containing extracts of mammalian brain have been commercially available for this purpose for some time. Platelets per se could be used, but these blood cells are storage unstable and not practical for commercial products.

The reagent should be buffered at a pH of about from 7 to 8, preferably pH 7.25 0.05. Suitable buffers will be apparent to the artisan. A preferred buffer is N-2-hydroxylethyl piperazine-$N^1$-2-ethane sulfonic acid.

The reagent also should contain an anti-microbial agent. These are well known and include such bacteriostats as phenol and sodium azide. These extend the shelf life of the reagent after it is opened.

The reagent need contain no suspending agent. These agents have been used commonly to maintain the homogeneity of activator particle suspensions; they exert no known biochemical activity in the clotting assays, their action being restricted to mechanical effects. The use of such agents in clotting assays are disclosed in U.S. Pat. No. 3,395,210.

The reagent may be used in any assay in which activation of Hageman factor is induced as part of the method, particularly the APTT test and its embodiments described above. In performing such tests the colloidal silica reagent herein is mixed with the test sample and a source of calcium ions and incubated until a clotting end-point is reached as determined by viscosity or other means as known in the art.

EXAMPLE 1

NALCOAG[R] 1060 colloidal silica was obtained from the Nalco Chemical Company. The colloidal particles in this product had a mean particle size of 60 m$\mu$ and a surface area of 50 m$^2$/gram. The colloidal silica was dispersed into 1020 ml of distilled water containing rabbit brain cephalin, 11.9 gm N-2-hydroxyethyl piperazine-N$^1$-2-ethane sulfonic acid and 1.5 gm phenol until a particle concentration of about 0.1% w/v was obtained. This reagent could be stored unopened for greater than three weeks, up to six months to a year, without agglomerating or otherwise failing to perform satisfactorily. It was used in an APTT test as follows: 0.1 ml of test plasma was pipetted into a cuvette or test tube. The reagent was agitated and 0.1 ml added to the specimen container. The mixture was incubated for exactly 5 minutes, after which 0.1 ml of 0.025 M calcium chloride at 37° C. was added. The clotting time for the test specimen was recorded. The mean clotting times to the nearest 0.1 seconds for duplicate determinations were reported as the activated partial thromboplastin time. The day-to-day and within-day reproducibility of this assay was satisfactory.

EXAMPLE 2

Example 1 was repeated except that the particles used were alumina-coated silica from the Nalco Chemical Company having a mean diameter of 70 m$\mu$ and a surface area of less than 50 m$^2$/gram.

The performance of the assay was compared with that of commercially available APTT tests using a reconstituted, lyophilized preparation containing fumed silica as the contact activator (General Diagnostics) and another using an aqueous solution of sodium ellagate as activator (Dade, Actin reagent). The within-run precision of the three tests were compared by running on two different instruments (BBL Fibrometer and Lancer Coagulyzer instruments) 20 consecutive determinations each on pooled normal and pooled abnormal coagulation controls (OMEGA TM Level 1 and level 2 controls, Hyland Diagnostics Division of Travenol Laboratories, Inc.). The day-to-day precision of the three tests were compared by running the above controls on the same instruments in duplicate on each of ten days. The results are tabulated below:

TABLE I

| | Within-Day Precision Study on Normal Coagulation Control | | | | | | | | |
|---|---|---|---|---|---|---|---|---|---|
| | Alumina-coated Silica | | | Fumed Silica | | | Sodium Ellagate | | |
| Instrument | Mean (Seconds) | Standard Deviation | % C.V. | Mean (Seconds) | Standard Deviation | % C.V. | Mean (Seconds) | Standard Deviation | % C.V. |
| BBL Fibrometer | 30.0 | 0.2 | 0.8 | 28.1 | 0.3 | 0.9 | 26.6 | 0.3 | 1.1 |
| Lancer Coagulyzer | 28.8 | 0.3 | 0.9 | 27.6 | 0.2 | 0.7 | 22.5 | 0.3 | 1.1 |

TABLE II

| | Within-Day Precision Study on Abnormal Coagulation Control | | | | | | | | |
|---|---|---|---|---|---|---|---|---|---|
| | Reagent | | | | | | | | |
| | Alumina-coated Silica | | | Fumed Silica | | | Sodium Ellagate | | |
| Instrument | Mean (Seconds) | Standard Deviation | % C.V. | Mean (Seconds) | Standard Deviation | % C.V. | Mean (Seconds) | Standard Deviation | % C.V. |
| BBL Fibrometer | 79.8 | 0.5 | 0.6 | 67.7 | 1.0 | 1.5 | 70.6 | 0.8 | 1.1 |
| Lancer Coagulyzer | 77.1 | 1.1 | 1.4 | 62.1 | 0.4 | 0.6 | 52.1 | 0.4 | 0.8 |

TABLE III

| | Day-to-Day Precision Study on BBL Fibrometer Instrument | | | | | | | | |
|---|---|---|---|---|---|---|---|---|---|
| | Reagent | | | | | | | | |
| | Alumina-coated Silica | | | Fumed Silica | | | Sodium Ellagate | | |
| Control | Mean (Seconds) | Standard Deviation | % C.V. | Mean (Seconds) | Standard Deviation | % C.V. | Mean (Seconds) | Standard Deviation | % C.V. |
| OMEGA TM Coagulation Control-Citrate Level 1-Normal | 30.7 | 0.5 | 1.5 | 28.3 | 0.7 | 2.3 | 29.4 | 1.6 | 5.4 |
| OMEGA TM Coagulation Control-Citrate Level 2-Abnormal | 79.3 | 2.1 | 2.6 | 66.8 | 2.1 | 3.1 | 76.3 | 3.8 | 5.0 |

The above data demonstrate the improved efficacy of the silica and alumina-coated colloidal silica reagent herein. Particularly noteworthy is the reduced percent coefficient of variation in day-to-day practice of the improved activator reagent of this invention when compared with another liquid reagent, sodium ellagate, and the favorable results in comparison with a fumed silica reagent that was disadvantageous because it required reconstitution before use.

What is claimed is:

1. A reagent in determining clotting factor in blood comprising water, a substance having blood platelet factor activity and colloidal silica or colloidal alumina-coated silica particles of about from 4 to 100 mµ mean diameter, said silica particles having been obtained by a process comprising (a) contacting on alkali silicate solution with an ion-exchange material for removing alkali metal ions from the silicate solution, and (b) recovering the colloidally dispersed particles from the ion exchange material.

2. The reagent of claim 1 wherein the particles are about from 60 to 70 mµ mean diameter.

3. The reagent of claim 1 wherein the particles are alumina-coated silica of about 70 mµ mean diameter and having a surface area of less than about 50 $m^2$/gram.

4. The reagent of claim 1 which is substantially free of suspending agents.

5. The reagent of claim 1 which additionally comprises an antimicrobial agent and a buffer.

6. A method for preparing a reagent for use in determining clotting factor in blood which comprises combining water, a substance having blood platelet factor activity and colloidal silica or alumina-coated colloidal silica particles of about from 4 to 100 mµ mean diameter, said silica particles having been obtained by a process comprising (a) contacting an alkali silicate solution with an ion-exchange material for removing alkali metal ions from the silicate solution, and (b) recovering the colloidally dispersed particles from the ion exchange material, placing the combination into containers, sealing the containers and storing the containers for at least about three weeks.

7. The method of claim 6 wherein the containers are stored for at least about six months.

8. In a method for determining the ability of blood or a blood derivative to clot wherein Hageman factor is activated with a contact activator, the improvement comprising using as said contact activator colloidal silica or colloidal alumina-coated silica particles of about from 4 to 100 mµ mean diameter, said silica particles having been obtained by a process comprising (a) contacting an alkali silicate solution with an ion-exchange material for removing alkali metal ions from the silicate solution, and (b) recovering the colloidally dispersed particles from the ion exchange material.

9. The method of claim 8 wherein the particles are about from 60 to 70 mµ mean diameter.

10. The method of claim 8 wherein the particles are alumina-coated silica of about 70 mµ mean diameter and having a surface area of less than about 50 $m^2$/gram.

* * * * *